(12) United States Patent
Yoshifusa et al.

(10) Patent No.: US 8,613,878 B2
(45) Date of Patent: Dec. 24, 2013

(54) MEDICAL ELONGATE MEMBER, METHOD OF MANUFACTURING THE SAME, AND APPARATUS FOR MANUFACTURING THE SAME

(75) Inventors: Yuuki Yoshifusa, Fujinomiya (JP); Terunobu Mochizuki, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 670 days.

(21) Appl. No.: 12/341,511

(22) Filed: Dec. 22, 2008

(65) Prior Publication Data
US 2009/0171320 A1 Jul. 2, 2009

Related U.S. Application Data

(60) Provisional application No. 61/064,137, filed on Feb. 19, 2008, provisional application No. 61/064,332, filed on Feb. 28, 2008, provisional application No. 61/016,749, filed on Dec. 26, 2007, provisional application No. 61/006,678, filed on Jan. 25, 2008.

(30) Foreign Application Priority Data

Dec. 27, 2007 (JP) ................................ 2007-338104
Jan. 25, 2008 (JP) ................................ 2008-015153

(51) Int. Cl.
*B29C 43/00* (2006.01)

(52) U.S. Cl.
USPC ........... 264/293; 425/406; 425/385; 425/392; 425/402

(58) Field of Classification Search
USPC .............. 264/293; 425/406, 385, 392, 402
See application file for complete search history.

(56) References Cited

U.S. PATENT DOCUMENTS

| | | | |
|---|---|---|---|
| 2,233,869 A * | 3/1941 | Lukacs | ........................ 72/31.07 |
| 2,654,124 A | 10/1953 | Layte | |
| 4,109,356 A * | 8/1978 | Mazzone | ........................ 28/279 |
| 4,283,824 A * | 8/1981 | Schatz et al. | ............. 29/890.045 |
| 4,898,702 A * | 2/1990 | Elkins et al. | .................. 264/145 |
| 5,507,995 A | 4/1996 | Schweich, Jr. et al. | |
| 5,681,296 A | 10/1997 | Ishida | |
| 6,117,383 A | 9/2000 | Kirschbaum | |
| 6,251,085 B1 | 6/2001 | Tezuka | |
| 6,390,992 B1 | 5/2002 | Morris et al. | |

(Continued)

FOREIGN PATENT DOCUMENTS

| | | |
|---|---|---|
| JP | 62-267132 a | 11/1987 |
| JP | 2-40992 Y2 | 10/1990 |
| JP | 8-266635 A | 10/1996 |
| JP | 9-117967 A | 5/1997 |
| JP | 10-118188 A | 5/1998 |
| JP | 3394327 B2 | 4/2003 |
| WO | WO 2006/065356 A1 | 6/2006 |

OTHER PUBLICATIONS

Takahane et al., "Production of Squeezed Hollow Foam", JP 09-117967 machine translation.*

(Continued)

*Primary Examiner* — Galen Hauth
(74) *Attorney, Agent, or Firm* — Buchanan Ingersoll & Rooney PC

(57) ABSTRACT

Disclosed herein is a medical elongate member including a elongate base material, a resin layer formed to coat or to be integral with the surface of at least a part of the base material, and a plurality of projections dispersed uniformly in a surface of the resin layer.

20 Claims, 18 Drawing Sheets

(56) References Cited

U.S. PATENT DOCUMENTS

| | | | |
|---|---|---|---|
| 2003/0125762 A1* | 7/2003 | Eidenschink | 606/194 |
| 2004/0167439 A1 | 8/2004 | Sharrow | |
| 2005/0096665 A1 | 5/2005 | Reynolds | |
| 2005/0148865 A1 | 7/2005 | Weber | |
| 2006/0073264 A1 | 4/2006 | Sakane et al. | |
| 2006/0173421 A1 | 8/2006 | Weber et al. | |
| 2006/0211952 A1 | 9/2006 | Kennedy, II | |
| 2006/0267245 A1* | 11/2006 | Halbeisen et al. | 264/284 |
| 2007/0184265 A1* | 8/2007 | Ranganathan et al. | 428/375 |
| 2007/0255217 A1 | 11/2007 | Burkett et al. | |
| 2007/0299402 A1 | 12/2007 | Ishii et al. | |
| 2008/0097213 A1 | 4/2008 | Carlson et al. | |

OTHER PUBLICATIONS

International Search Report and Written Opinion (Forms PCT/ISA/210 and PCT/ISA/237) issued in PCT/JP2008/073123, Apr. 7, 2009; and English-language translation thereof.

Extended European Search Report issued Dec. 22, 2011 by the European Patent Office in European Application No. 08864849.8.

Office Action issued by Japan Patent Office on Jan. 29, 2013 in corresponding Japanese Patent Application No. 2009-547069, and English translation thereof.

* cited by examiner

144

10

MEDICAL ELONGATE MEMBER, METHOD OF MANUFACTURING THE SAME, AND APPARATUS FOR MANUFACTURING THE SAME

BACKGROUND OF THE INVENTION

1. Field of the Invention

The present invention relates to a medical elongate member, a method of manufacturing the same, and an apparatus for manufacturing the same.

2. Description of the Related Art

A variety of medical elongate members such as guide wires and catheters are employed for various uses such as examinations of living bodies, treatments, etc.

Catheters are used in treatment of portions at which open surgeries are difficult or which require minimal invasiveness to the body, for example, PTCA (Percutaneous Trasluminal Coronary Angioplasty), or in examination such as cardioangiography. Guide wires are used to guide a catheter to the objective cite in the living body.

A guide wire used in PTCA is inserted, with its distal end protruding from the distal end of a balloon catheter, into the vicinity of the target stenosis portion together of its coronary with the balloon catheter. The thinner guide wire is first passed through the stenosis part, so as to guide the balloon catheter while widening the stenosis portion. In the case of PTA (Percutaneous Treansluminal Angioplasty), also, the guide wire is used to guide the balloon catheter to a stenosis portion, like in PTCA, in order to achieve recanalization of a stenosis/occulusion portion of a femoral, iliac, renal, shunt or other peripheral blood vessel.

A guide wire is inserted into the lumen of a catheter or the inner cavity of an endoscope and is moved in its longitudinal direction or rotated in use. In this case, a lower sliding resistance (lower frictional resistance) is preferred for attaining enhanced steerability of the guide wire.

From this point of view, there has been proposed a guide wire in which a fluororesin coating layer containing a particulate material added thereto is formed on the surface of a metallic wire (See FIGS. 1 and 2 of US patent Publication No. 2006-0073264 A1). According to the guide wire, a plurality of projections are formed in the surface of the fluororesin coating layer due to the presence of the particulate material. Therefore, the area of contact of the guide wire with the inner surface of the catheter is reduced, whereby the frictional resistance is lowered.

In the guide wire described in U.S. patent Publication No. 2006-0073264 A1, however, it happens the distribution of the particulate material in the surface of the fluororesin coating layer is not uniform. Therefore, the frictional resistance of the guide wire may vary locally or may vary from product to product. This makes difficult the operation (steering) of the guide wire, which relies on subtle sensation.

In addition to the above, there has also been proposed a guide wire in which a plurality of metallic wires are bundled and twisted and a fluororesin coating layer is formed on the surface of the twisted bundle so as to reduce the area of contact with the inner surface of a catheter (See FIG. 2 of patent No. U.S. Pat. No. 6,251,085 B1).

In the guide wire described in patent No. U.S. Pat. No. 6,251,085 B1, however, not the fluororesin coating layer on the surface but the metallic wires themselves fundamental to the guide wire are worked. Consequently, the guide wire obtained shows a weakened durability.

SUMMARY OF THE INVENTION

It is an object of the present invention to provide a elongate member having projections distributed uniformly in the surface thereof while retaining high durability.

It is another object of the present invention to provide a elongate member the surface of which has a uniform smoothness over the entire area thereof.

A medical elongate member according to the present invention includes a elongate base material, a resin layer formed to coat or to be integral with the surface of at least a part of the base material, and a plurality of projections distributed uniformly in a surface of the resin layer.

Another medical elongate member according to the present invention includes a elongate base material, and a resin layer which is formed to coat or to be integral with the surface of at least a part of the base material and which has a plurality of projections at the surface thereof, the resin layer having an SMD of 0.22 to 0.48 μm throughout the surface thereof.

A method of manufacturing a medical elongate member includes the following steps. First, a elongate member having a surface formed of a resin is prepared. A first die roller which is rotatable about a first rotational axis inclined against the axial direction of the elongate member and which is provided with recesses in a cylindrical side surface thereof and a second die roller which is rotatable about a second rotational axis inclined against the axial direction of the elongate member and crossing the first rotational axis and which is provided with recesses in a cylindrical side surface thereof are arranged so as to clamp the elongate member therebetween. A rugged surface pattern corresponding to the recesses in the first die roller and the second die roller are formed on the elongate member by rotating the first die roller and the second die roller and feeding the elongate member along the axial direction thereof.

Another method of manufacturing a medical elongate member includes the following steps. First, an elongate member having a surface formed of a resin is prepared. A pair of die rollers each of which is rotatable about a rotational axis perpendicular to the axial direction of the elongate member and is provided with recesses in a cylindrical side surface thereof are arranged so as to clamp the elongate member therebetween. A rugged surface pattern corresponding to the recesses in the pair of the die rollers is formed on the elongate member by rotating the pair of rollers and feeding the elongate member along the axial direction thereof.

Further objects, features and advantages of the present invention will become apparent from a study of the preferred embodiments illustratively described below.

DETAILED DESCRIPTION OF THE PREFERRED EMBODIMENTS (First Embodiment)

Figure 1:
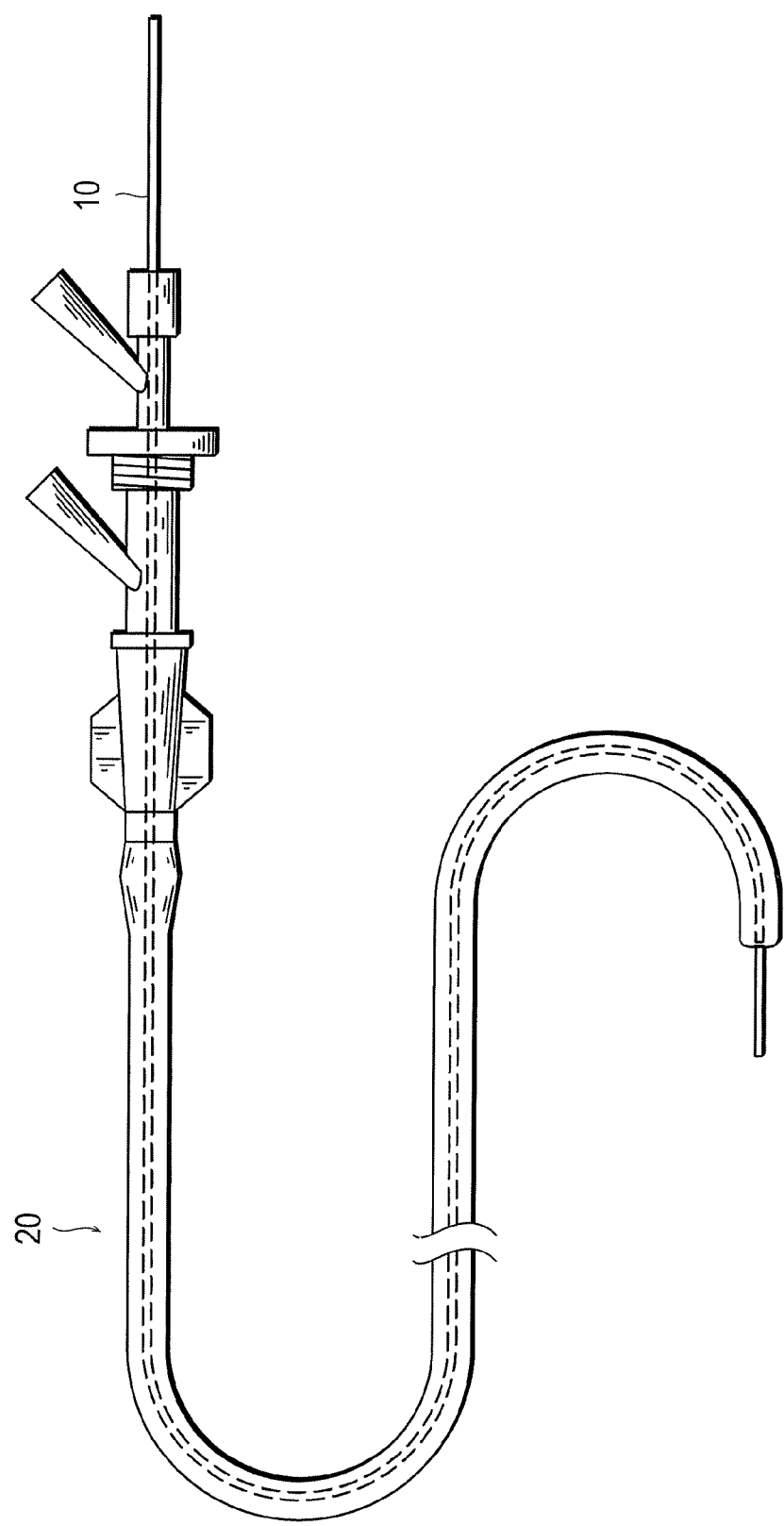
FIG. 1 is a schematic view showing the configuration of a catheter.
Figure 2A:
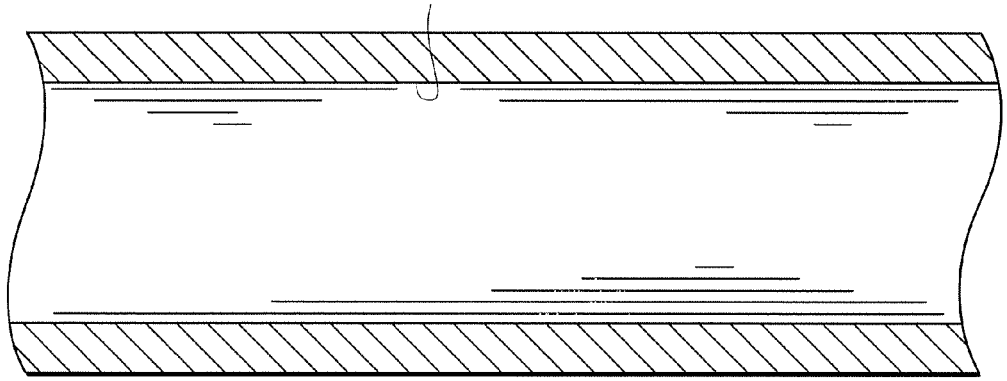
FIGS. 2A and 2B are partial sectional views of the catheter.
Figure 2B:
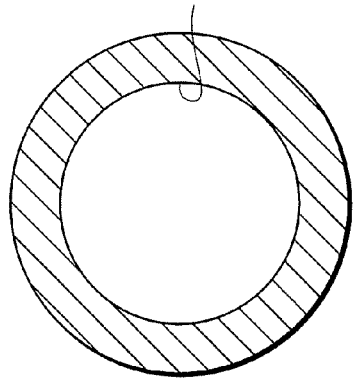

FIG. 1 is a schematic view showing a guide wire inserted in a catheter, FIGS. 2A and 2B show partial sectional views of the catheter. Incidentally, FIG. 2A is a sectional view taken in parallel to the axial direction of the catheter, and FIG. 2B is a sectional view taken perpendicularly to the axial direction of the catheter.

As shown in FIG. 1, the guide wire 10 is capable of passing through a lumen formed along the axial direction in the inside of the catheter 20. An operator can move the guide wire 10 distally and proximally (forwards and backwards) in the catheter 20 by holding the proximal end of the guide wire 10 and moving it distally and proximally.

The catheter 20 has a flexible tubular body, and, as shown in FIGS. 2A and 2B, is provided with a lumen 22 in its substantially central part and over the whole length of its body. The catheter 20 is inserted, for example, into a blood vessel in a living body and is guided to a diseased portion by the guide wire 10. There are a variety of catheters, including angiography catheter, micro-catheter, balloon catheter, intracardiac catheter, pulmonary catheter, and urethral catheter. Any general catheter may be used. Here, detailed description of the functions of the catheter is omitted.

Figure 3:
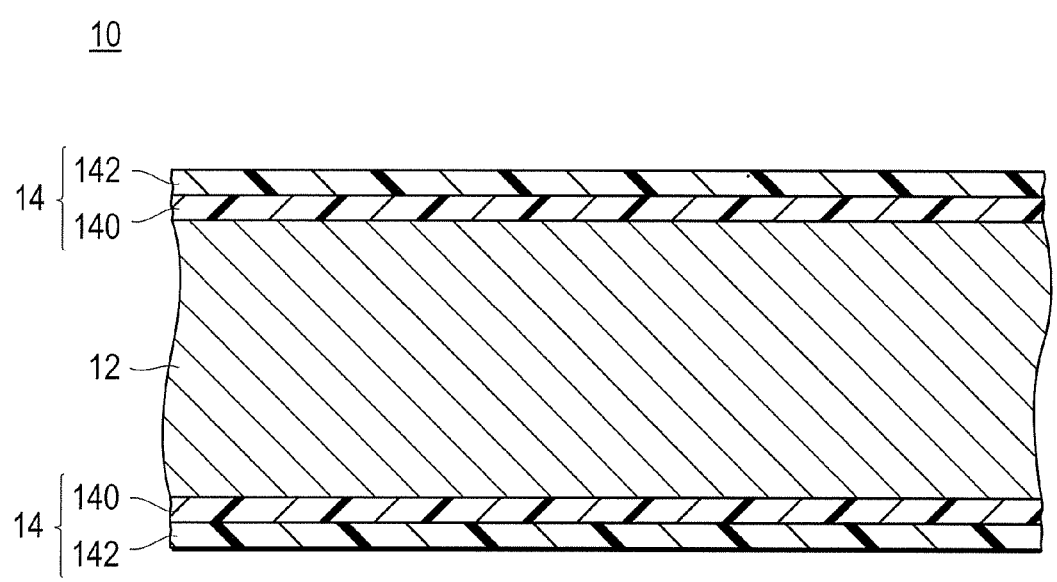
FIG. 3 is a sectional view of a guide wire.
Figure 4:
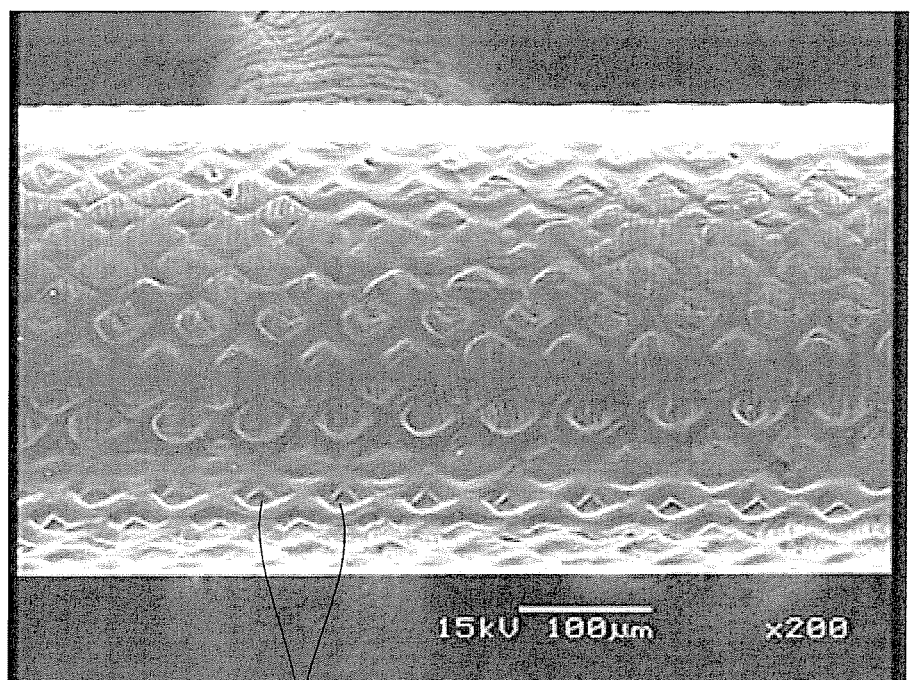
FIG. 4 is an enlarged view showing the surface shape of the guide wire.
Figure 5:
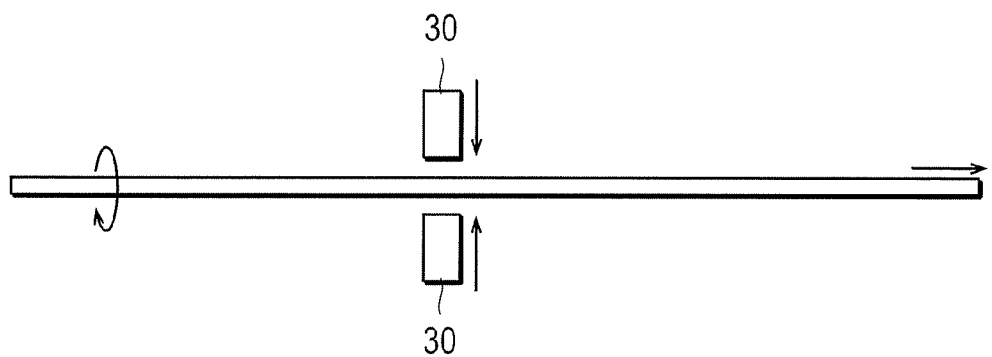
FIG. 5 is a schematic view showing an apparatus for working a guide wire.
Figure 6:
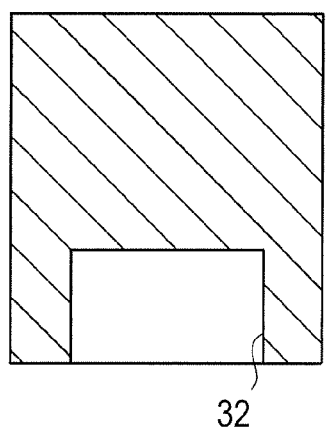
FIG. 6 illustrates a die in the working apparatus.
Figure 7:
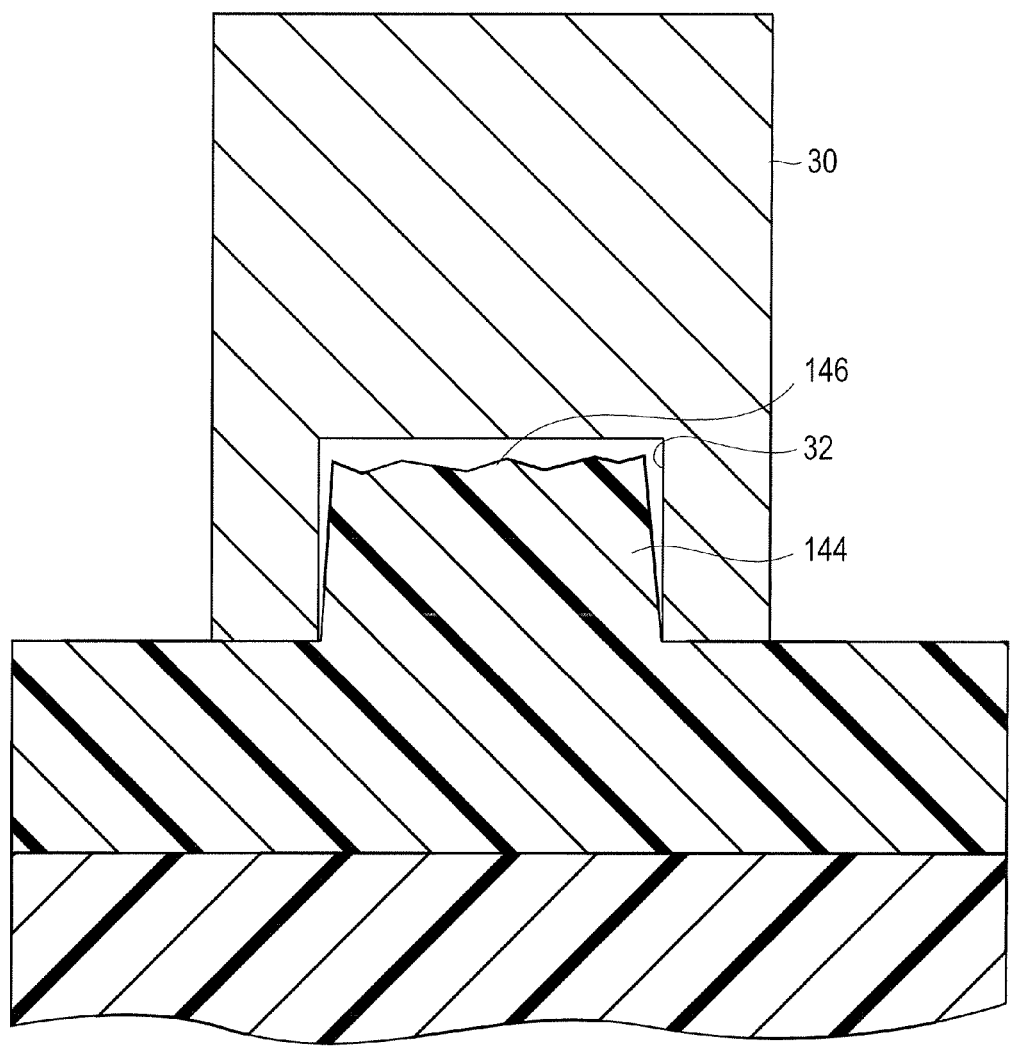
FIG. 7 illustrates the manner in which a resin layer is formed inside the die.

FIG. 3 is a sectional view of a guide wire, FIG. 4 is an enlarged view showing the surface shape of the guide wire, FIG. 5 is a schematic view showing an apparatus for working a guide wire, FIG. 6 illustrates a die of the working apparatus, and FIG. 7 illustrates the manner in which a resin layer is deformed in the die.

The guide wire 10 is a medical implement preliminarily advanced inside a blood vessel of a living body, for example, for guiding a catheter inserted in the blood vessel to a target site (diseased portion). The guide wire 10 can be inserted in the lumen formed along the axial direction in the inside of the catheter. Therefore, the catheter can be advanced inside the blood vessel along the guide wire 10.

As shown in FIG. 3, the guide wire 10 has a multilayer structure. The guide wire 10 includes a single filamentous wire 12 which is formed of a single material, for example, nickel titanium, and a resin layer 14 which is formed from resin to coat the surface of the wire (base material) 12. The resin layer 14 includes a primer layer 140 coating the wire 12 in intimate contact, and a fluororesin layer 142 formed from a fluorine-containing resin to coat the primer layer 140.

Examples of a material of the wire 12 include stainless steels, cobalt alloys instead of Ni—Ti alloys. Examples of the primer layer 140 of the resin layer 14 include polysulfone, polyimide, polyamide-imide, epoxy resin, phenolic resin. The fluororesin layer 142 is formed from PTFE, PFA, FEP. A surface layer of the primer layer 140 may be formed from for example polyamide, polyethylene, silicone, polyurethane instead of the fluororesin layer 142. Not shown in figure, the resin layer 14 may be formed of a single layer. The resin layer 14 is made by not only coating, but also shrinking the fluororesin shrink tube formed from PTFE,PFA,FEP etc.

The guide wire 10 has at least its surface formed from resin.

Though omitted in FIG. 3, a plurality of fine projections 144 are formed in the surface of the fluororesin layer 142. As shown in FIG. 4, the projections 144 are distributed uniformly in the surface of the resin layer 14.

In forming such projections 144, use of a working apparatus as shown in FIG. 5 may be contemplated. The working apparatus shown in FIG. 5 has a pair of dies 30 arranged symmetrically on opposite sides of the guide wire 10. The dies 30 are each provided with recesses 32, as shown in FIG. 6. In the working apparatus, the dies 30 are pushed toward each other from both sides of the guide wire 10 so that their surfaces provided with the recesses 32 are pressed against the guide wire 10. For example in the case where the diameter of the guide wire 10 is 0.014 inch, the pressure with which the dies 30 are pushed toward each other is 300 to 1200 gf, preferably 400 to 600 gf.

The dies 30 are being heated to a temperature of not higher than the melting point of the resin layer 14. Due to the heating, the resin layer 14 at the surface of guide wire 10 is easily deformed, resulting in formation of the projections 144. The heating temperature for the dies 30 is, for example, 80 to 260° C., preferably 180 to 220° C. It is to be noted here, however, that the melting point of the resin layer 14 varies depending on the components thereof, and, therefore, the heating temperature may be changed, as required, according to the resin components.

The recesses 32 in the dies 30 are not provided with passages for permitting air to escape, i.e., so-called air vents, in their bottom parts. Therefore, as shown in FIG. 7, the resin of the resin layer 14 (fluororesin layer 142) flows into the recess 32 only to such an extent as to incompletely fill the recess 32. Accordingly, as shown in the figure, the projection 144 has primarily an upper surface which is not flat but is provided with finer ruggedness (finer recesses and projections) 146. Or, alternatively, the recesses 32 of the dies 30 may be provided with air vents. In that case, air can escape, so that the resin of the resin layer 14 flows into the recesses 32 of the dies 30 so as to completely fill up the recesses 32. Thus, projections 144 having flat top faces can also be formed.

In the working apparatus, the pressing operation as above-mentioned is carried out while rotating the guide wire 10 until the projections 144 are formed in the whole circumference of the guide wire 10, in other words, until the guide wire 10 is rotated by about 180 degrees. After the projections 144 are formed in the whole circumference, the working apparatus feeds the guide wire 10 by a predetermined amount by a feeding device (not shown), and the projections 144 are formed in the whole circumference. The predetermined amount here is, for example, such a distance that the projections 144 formed will not be broken at the time of the next working action of the dies 30. This treatment is repeated, whereby the projections are formed in the whole circumference over the entire length of the guide wire 10.

Incidentally, in the above description, elliptic projections 144 are formed in the surface of the guide wire 10, as shown in FIG. 4. It should be noted, however, the shape of the projections 144 in top plan view is not limited to an ellipse, and may be any other shape such as circle and polygon. Further, in the case of forming the projections by heat transfer, the guide wire surface upon working may be a satin-finished surface obtained through transfer by use of dies which have satin-finished surfaces.

In this manner, a plurality of projections 144 are formed in the surface of the guide wire 10 in a uniformly distributed state. Here, the size and distribution of the projections 144 are so determined that the SMD is 0.26 to 0.48 μm, preferably 0.38 to 0.46 μm.

SMD stands for mean deviation of surface geometrical roughness, which can be measured by the method described later. When the SMD exceeds 0.48 μm, the surface ruggedness is so rough and the frictional coefficient is so high that the insertion resistance in use will be too high. On the other hand, when the SMD is below 0.26 μm, the surface ruggedness is smaller and the frictional coefficient is all the more higher, so that the insertion resistance in use will be higher. It is more preferable that the SMD is 0.38 to 0.42 μm.

The size and distribution of the projections 144 for obtaining a desired SMD can be computed, for example, by computer simulation. As another method, try-and-error determination of optimal parameters may be adopted. Specifically, guide wires 10 are manufactured by way of trial while regulating the size of the recesses 32 in the dies 30, the interval in pressing the dies, the pressing pressure, etc., and the guide wires 10 obtained are subjected to measurement of SMD of their surface. When a guide wire 10 with an SMD of 0.38 to 0.46 μm is obtained, the parameters such as the size of the recesses 32 in the dies 30, the interval in pressing the dies, the pressing pressure, etc. in that run are recorded. The parameters thus recorded are employed in the subsequent runs of working, whereby the size and distribution of the projections 144 can be determined univocally.

Now, the method of measuring the SMD will be described.

The SMD is measured by use of a friction tester KES-SE (product name), produced by KATO TECH CO., LTD., compliant with the method described in Sueo Kawabata, "Standardization and Analysis for Evaluation of Feeling," 2nd ed., the Textile Machinery Society of Japan, 1980.

Specifically, both ends of three guide wires 10 arrayed laterally at intervals of 1 mm are fixed to glass preparations. While exerting a load of 10 gf from a direction perpendicular to the axial direction of the guide wires 10, a piano wire-made U-shaped contactor with a diameter of 0.5 mm is brought into contact with the guide wires 10. The contactor is fed at a rate of 1 mm/sec for 20 second. The vertical vibration of the contactor due to the projections 144 in the surface of the guide wires 10 is detected, and the vibration amplitude is integrated along the moving direction, to obtain the SMD. Thus, the SMD is expressed by the following formula.

$$SMD = \frac{1}{x} \int_0^x |T - \overline{T}| dx$$

T: thickness detected (μm)
$\overline{T}$: mean thickness (μm)
x: distance traveled (20 mm)
(Effects)

As above described, according to the first embodiment, a plurality of projections 144 distributed uniformly are formed in the surface of the resin layer 14. Therefore, when the guide wire 10 is inserted in the catheter 20, the area of contact with the inner surface of the catheter 20 is small. Consequently, a low sliding resistance is obtained uniformly over the entire part of the resin layer 14 of the guide wire 10.

In addition, according to the first embodiment, the plurality of projections 144 distributed uniformly are formed in the surface of the resin layer 14 so that the SMD is in the range of 0.22 to 0.48 μm. This ensures that a low sliding resistance is obtained uniformly over the entire part of the resin layer 14 of the guide wire 10. Since the SMD of the guide wire 10 is 0.22 to 0.48 μm, the operator can use any of the guide wires 10 with substantially the same sensation.

The surface roughness Rz of the plurality of projections 144 distributed uniformly in the surface of the resin layer 144, as measured under a laser microscope (VK-8500, produced by KEYENCE CORPORATION), is preferably 0.2 to 3 μm, more preferably 0.8 to 1.5 μm.

The density of the projections 144 is preferably not less than 15 projections per 0.04 mm$^2$, more preferably 20 to 60 projections per 0.04 mm$^2$.

The wire 12 is used without any special working applied thereto, except for the formation of the resin layer 14 on the surface thereof. Specifically, not any thermal influence that would change the physical properties of the wire 12 is generated in manufacturing the guide wire 10. Therefore, the product obtained shows high strength. In addition, not any external force such as torsion is applied to the wire 12, which also promises a high strength of the product.

As above-mentioned, in the case where no air vent is formed in the recesses 32 of the dies 30, the surfaces of the projections 144 are provided with finer ruggedness 146. Therefore, the area of contact between the guide wire 10 and the catheter 20 can be made smaller, and a lower sliding resistance can be obtained.

The resin layer 14 has a two-layer structure of the primary layer 140 and the fluororesin layer 142. Accordingly, the fluororesin layer 142 excellent in coating properties can be used as the outermost layer.

(Modification Examples of Guide Wire)

Now, modification examples of the guide wire will be described below.

(Modification Example 1 of Guide Wire)

In the first embodiment above, as shown in FIG. 7, the projections 144 have been tetragonal as views sideways in relation to the projecting direction.

Figure 8:
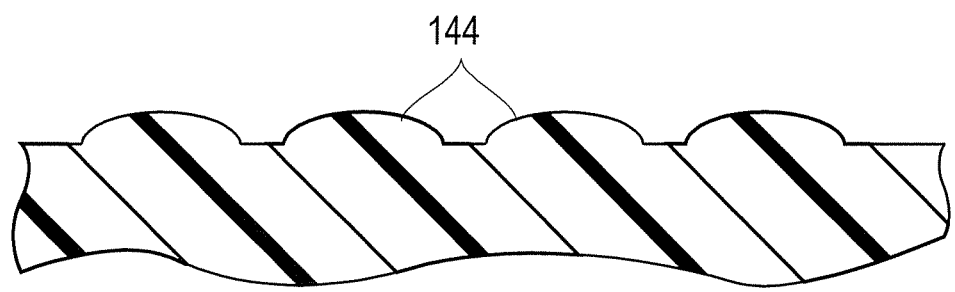
FIG. 8 illustrates hemispherical projections formed in the surface of a guide wire.

FIG. 8 illustrates hemispherical projections formed in the surface of a guide wire.

As shown in FIG. 8, the projections 144 may be formed in a hemispherical shape as viewed sideways in relation to the projecting direction. In this case, the recesses of the dies in the working apparatus are designed to be hemispherical in shape. Here, air vents are formed in the bottom parts of the recesses in the dies. Consequently, a shape of the projections 144 coinciding with the shape of the recesses in the dies can be obtained.

(Modification Example 2 of Guide Wire)

Figure 9:
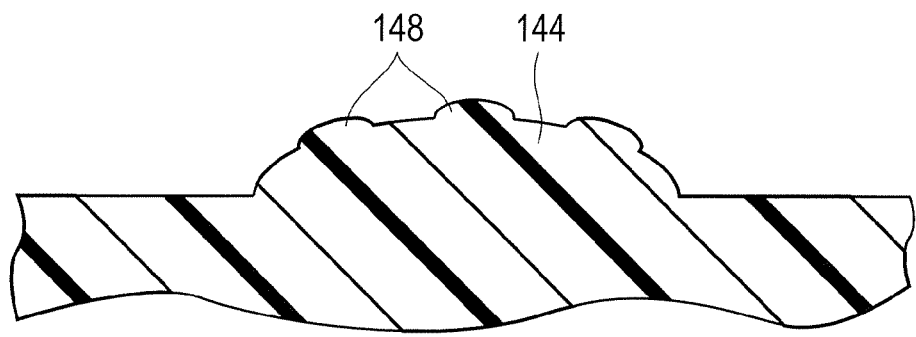
FIG. 9 illustrates another embodiment of the shape of the projections.
Figure 10:
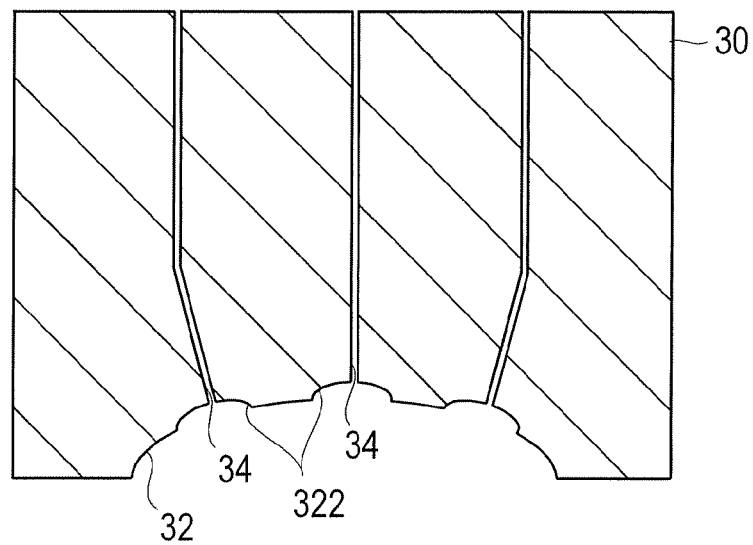
FIG. 10 is a sectional view of a die in the working apparatus.
Figure 11:
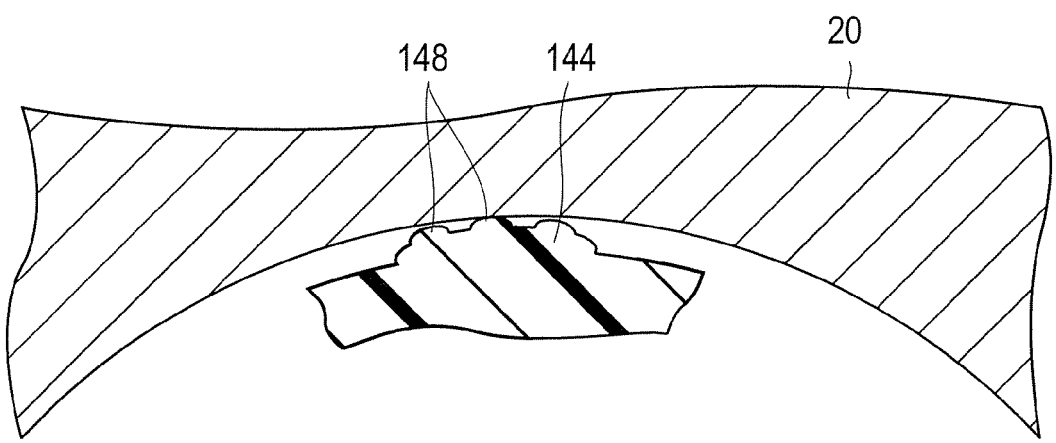
FIG. 11 illustrates the manner in which the projections make contact with the inner surface of a catheter.

FIG. 9 illustrates another embodiment of the shape of the projections, FIG. 10 is a sectional view of a die in the working apparatus, and FIG. 11 illustrates the manner in which the projections make contact with the inner surface of a catheter.

In Modification Example 2, the projections 144 are provided with finer projections 148 in their surfaces. For forming the finer projections 148, as shown in FIG. 10, the recesses 32 in the dies 30 of the working apparatus are each formed in a shape with which the projection 144 and the finer projections 148 coincide. Here, for the formation of the finer projections 148, the resin of the guide wire 20 has to flow into finer recesses 322. For this purpose, air vents 34 are formed at the recesses 32, particularly at the finer recesses 322, of the dies 30. This ensures that when the dies 30 are pressed against the guide wire 20, the resin can flow also into the finer recesses 322, whereby a projection shape as shown in FIG. 9 can be obtained.

Where the projections 144 are provided with finer projections 148 in this manner, only the finer projections 148 make contact with the inner surface of the catheter 20 even when the curvature of the surfaces of the projections 144 is equal to the curvature of the inner surface of the catheter 20, as shown in FIG. 11. As a result, the area of contact between the guide wire 10 and the catheter 20 is small, and the frictional resistance is small.

(Modification Example 3 of Guide Wire)

Figure 12:
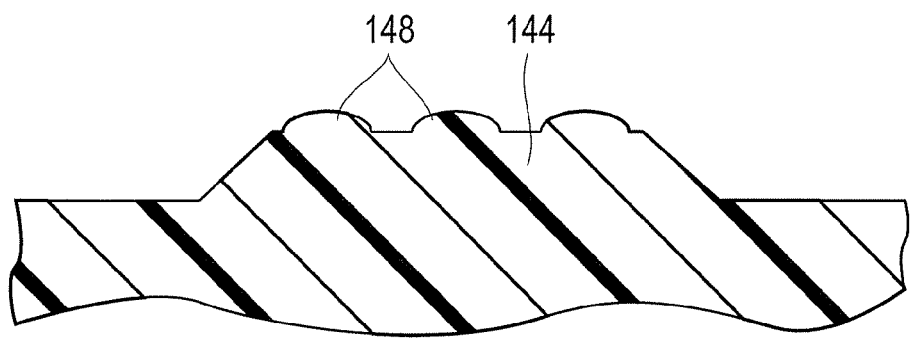
FIG. 12 illustrates a further embodiment of the shape of the projections.

FIG. 12 illustrates a further embodiment of the shape of the projections.

As shown in FIG. 12, the shape of the projections 144 may be a truncated cone or a truncated pyramid.

In this case, the top faces of the projections 144 are preferably provided with finer projections 148. The formation of the finer projections 148 can reduce the frictional contact between the outer surface of the guide wire 10 and the inner surface of the catheter 20.

Now, modification examples of the guide wire will be described below.

(Modification Example of Manufacturing Method)

In the embodiment above, a method has been described in which projections are transferred to the surface of an elongate member, in the manner of stamping, by pressing the dies 30 in the direction perpendicular to the axial direction of the elongate member. By improving this method, the following method may also be employed to form projections in the surface of an elongate member.

Figure 13:
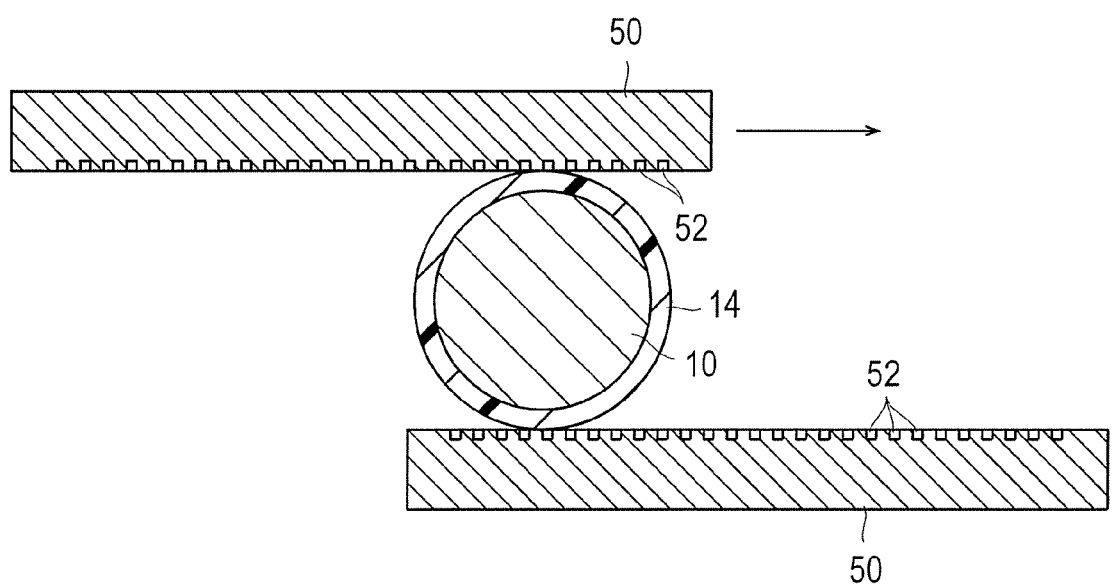
FIG. 13 is a schematic view showing a working apparatus for forming projections in the surface of an elongate member.

FIG. 13 is a schematic view showing a working apparatus for forming projections in the surface of an elongate member.

The working apparatus has two flat-surfaced dies 50 arranged so as to clamp a guide wire 10 (elongate member) therebetween. Of the two dies 50, one is fixed, whereas the other is slidable in the direction of arrow in the figure (a direction perpendicular to the axial direction of the guide wire 10) along the circumference of the guide wire 10. Each of the dies 50 is provided, in its surface on the side of the guide wire 10, with a plurality of recesses 52 arrayed in plural rows at regular intervals. The recesses 52 are formed in rows arrayed along the sliding direction of the die 50, and their shape coincides with the shape to be transferred to the resin layer 14 of the guide wire 10.

At the time of working, first, the dies 50 are heated to a temperature of 80 to 260° C., and are pressed to clamp the guide wire 10 therebetween with a force of 0.1 to 200 gf/mm². The die 50 on one side, for example, the die 50 on the upper side in the figure is slid in the direction of arrow by a distance equivalent to half the circumference of the guide wire 10. As a result, projections are transferred to the whole circumference of the guide wire 10 by the upper and lower dies 50. Subsequently, the guide wire 10 is moved by a predetermined distance in the axial direction thereof by a feeding device (not shown). This treatment is repeated, whereby the projections can be formed over the entire length of the guide wire 10.

Incidentally, while a process in which the transferring treatment is repeated has been described above, a plurality of rows of projections can be formed in the surface of the guide wire 10 through a single sliding operation of a die 50 by a method in which the die 50 prepared has a length corresponding to the axial length of the guide wire to be provided with the projections.

(Second Embodiment)

In a second embodiment, a mode in which the method and apparatus for manufacturing the guide wire in the fist embodiment are improved will be shown.

Figure 14:
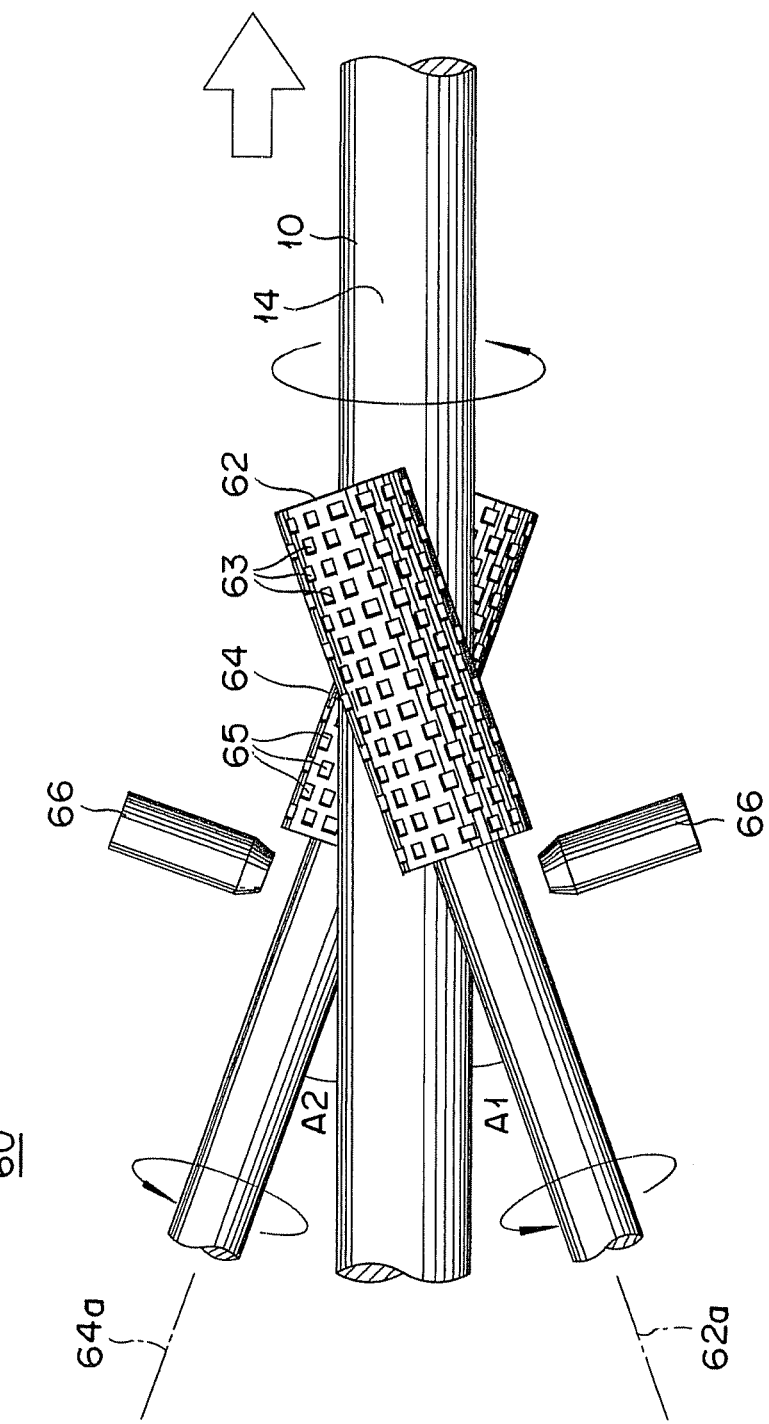
FIG. 14 illustrates an apparatus for manufacturing a medical elongate member.
Figure 15A:
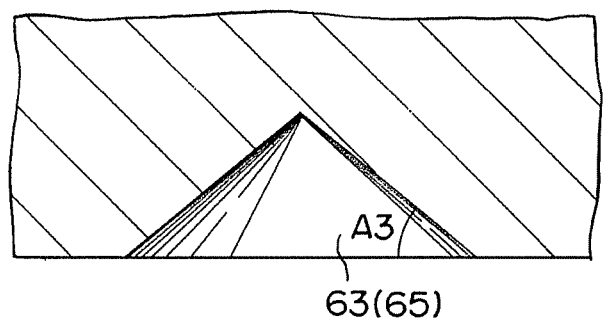
FIGS. 15A and 15B illustrate examples of the sectional shape of recesses in a die.
Figure 15B:
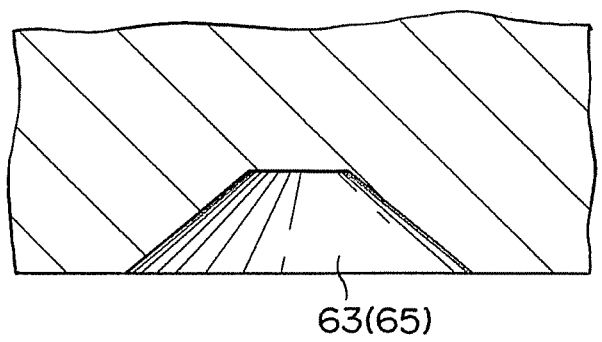
Figure 16:
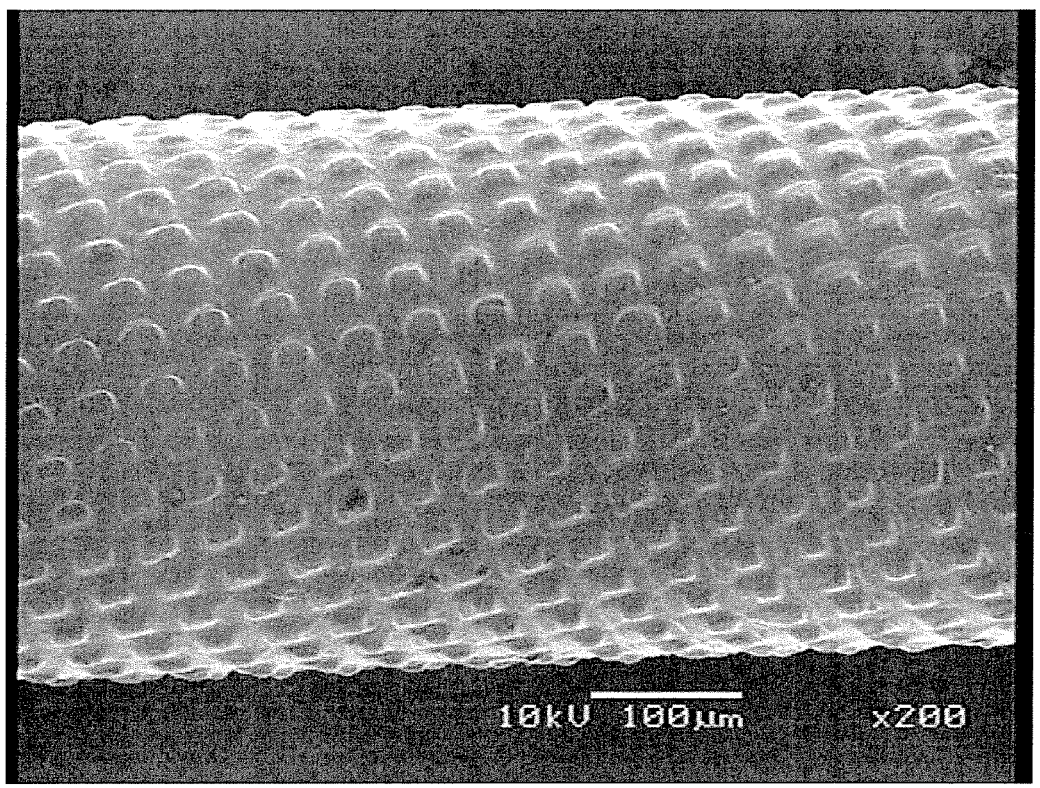
FIG. 16 is an enlarged view showing the surface shape of the medical elongate member.

FIG. 14 illustrates an apparatus for manufacturing a medical elongate member, and FIGS. 15A and 15B illustrate examples of the sectional shape of recesses in dies. FIG. 16 is an enlarged view showing the surface shape of the medical elongate member.

In this embodiment, a method and an apparatus for manufacturing a guide wire 10 as a medical elongate member will be described.

(Apparatus Configuration)

As shown in FIG. 14, the manufacturing apparatus 60 has a first die roller 62 and a second die roller 64. The first die roller 62 is cylindrical in shape, and is rotatable about a first rotational axis 62a inclined against the axial direction of a wire (hereinafter referred to also as "guide wire 10"). The first die roller 62 is provided with a plurality of recesses 63 in the cylindrical side surface thereof. The plurality of recesses 63 are distributed uniformly in the cylindrical side surface of the first die roller 62.

The second die roller 64 is cylindrical in shape, and is rotatable about a second rotational axis 64a which is inclined against the axial direction of the guide wire 10 and which crosses the first rotational axis 62a. The second die roller 64 is provided with a plurality of recesses 65 in the cylindrical side surface thereof. The plurality of recesses 65 are distributed uniformly in the cylindrical side surface of the second die roller 64. The second die roller 64 is provided at such a position as to be opposed to the first die roller 62 with the guide wire 10 therebetween. The first rotational axis 62a and the second rotational axis 64a are oriented in different directions.

The first rotational axis 62a and the second rotational axis 64a, preferably, form acute crossing angles A1, A2 with the axis of the guide wire 10. More preferably, the crossing angles A1 and A2 are not more than 10 degrees. Preferably, the crossing angles A1 and A2 are equal.

The recesses 63 in the first die roller 62 and the recesses 65 in the second die roller 64 may have any shape.

The shape of the recesses 63 and 65 is a pyramid such as a tetragon-based pyramid (square-based pyramid), for example. The recesses 63 and 65 are formed by cutting pyramids such as tetragon-based pyramids (square-based pyramids) out of the first die roller 62 and the second die roller 64. The shape is not limited to the tetragon-based pyramid but may be any pyramid, such as a triangle-based pyramid and a hexagon-based pyramid. Or, alternatively, the recesses 63 and 65 may be conical in shape. In this case, the recesses 63 and 65 are triangular in sectional shape, as shown in FIG. 15A.

Further, the shape of the recesses 63 and 65 may also be a truncated pyramid or a truncated cone, for example. In this case, the recesses 63 and 65 are trapezoidal in sectional shape, as shown in FIG. 15B. In the cases where the shape of the recesses 63 and 65 is a pyramid, a cone, a truncated pyramid or a truncated cone, the recesses 63 are each preferably so designed that the inclination angle A3 of a side surface of the recess relative to the major surface of the first die roller 62 is not more than 60 degrees. The same applies to the recesses 65, too. In the embodiment below, description will be made of the case where a tetragon-based pyramid is adopted as the shape of the recesses 63, 65.

The recesses 63 in the first die roller 62 and the recesses 65 in the second die roller 64 are preferably the same in shape. The recesses 63, 65 in the die rollers 62, 64 are preferably the same in distribution density.

The first die roller 62 and the second die roller 64 are each heated by a heating device 66 such as a glass torch. The heating temperature can be changed, as required, according to the material of the resin layer 14 of the guide wire 10 described later. The heating device may a heater embedded in the inside of each of the die rollers 62, 64.

(Manufacturing Procedure)

First, a wire 10 having a resin layer 14 at its surface is prepared. Then, a first die roller 62 and a second die roller 64 are arranged so as to clamp the guide wire 10 therebetween.

The first die roller 62 and the second die roller 64 are heated by glass torches 66 to a temperature of not lower than the glass transition point (or, in the case of an amorphous resin, the softening point thereof) of the resin layer 14 at the surface of the guide wire 10.

The first die roller 62 and the second die roller 64 are rotated respectively about a first rotational axis 62a and a second rotational axis 64a as indicated by arrows in FIG. 14. Attendant on this, the guide wire 10 is fed in the direction of large arrow in FIG. 1 while being rotated as indicated by arrow in FIG. 1. In this case, projections corresponding to the shape of recesses 63 of the first die roller 62 are formed in the resin, softened by heat, at the surface of the guide wire 10. Similarly, projections are formed in the surface of the guide wire 10 by recesses 65 of the second die roller 64.

Since the guide wire 10 is fed as the first die roller 62 and the second die roller 64 are rotated, the first die roller 62 and the second die roller 64 are sequentially brought into contact with different positions of the surface of the guide wire 10. Consequently, the projections are successively formed in the surface of the guide wire 10.

In this manner, the projections are formed in the surface of the guide wire 10 uniformly in a predetermined pattern, as shown in FIG. 16. The projections are helically arrayed in the surface of the guide wire 10. Specifically, the resin layer 14 is provided with a multiplicity of helical arrays of the projections. The multiplicity of helical arrays of the projections has lower contact area to the rumen of the catheter when the guide wire 10 is moved towards the axis thereof. Then the guide wire 10 may be easily inserted.

(Effects)

As above-described, according to the second embodiment, the first rotational axis 62a of the first die roller 62 and the second rotational axis 64a of the second die roller 64 cross each other by way of the guide wire 10 therebetween. Therefore, by only rotating the first die roller 62 and the second die roller 64, the projections are successively formed in the surface of the guide wire 10 while the guide wire 10 is fed automatically. With the above-mentioned method and apparatus used, very good productivity is ensured even when the medical elongate member such as a guide wire is comparatively long.

The first rotational axis 62a and the second rotational axis 64a form acute crossing angles A1, A2 with the axis of the guide wire 10. Therefore, the guide wire 10 can be fed appropriately.

The recesses 63, 65 in the first die roller 62 and the second die roller 64 are formed in the shape of a pyramid, a cone, a truncated pyramid or a truncated cone. Particularly, when the inclination angle A3 of the side surfaces of the recesses relative to the major surface of the first die roller 62 is not more than 60 degrees, there is no edge that hooks the resin having entered the recesses 63, 65. This ensures that when the recesses 63, 65 part from the guide wire 10, there is no possibility that the projections formed at the surface layer of the resin layer 14 might be caught (hooked) on edges and broken. Thus, the peel strength of the projections is enhanced.

Since the first die roller 62 and the second die roller 64 are being heated, the shape of the recesses 65 can be easily transferred to the resin of the resin layer 14.

(Modification Example of Second Embodiment)

In the second embodiment above, an example in which the first die roller 62 and the second die roller 64 are provided respectively with the recesses 63 and 65 has been described. However, this configuration is not limitative. The first die roller and the second die roller may be modified as follows.

Figure 17:
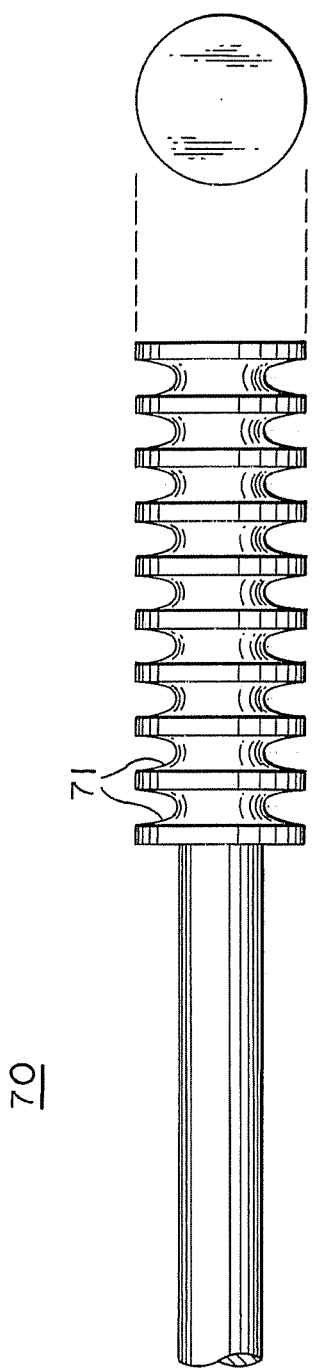
FIG. 17 illustrates a modification example of a first die roller and a second die roller.
Figure 18:
FIG. 18 is a schematic view showing the finished shape of a formed guide wire 10.

FIG. 17 illustrates a modification of the first die roller and the second die roller, FIG. 18 is a schematic view showing the finished shape of the guide wire 10 formed.

A die roller 70 shown in FIG. 17 may be used in place of each of the first die roller 62 and the second die roller 64 in FIG. 14. The die roller 70 is provided with grooves 71 along the circumferential direction of a cylindrical side surface thereof. In this point, the die roller 70 is different from the first die roller 62 and the second die roller 64 in the first embodiment.

The die rollers 70 thus prepared for replacement of the die rollers 62, 64 are applied to the manufacturing apparatus 60 in FIG. 14. The two die rollers 70 are arranged so that their rotational axes cross each other by way of the axis of the guide wire 10 therebetween when the die rollers 70 are rotated as the first die roller and the second die roller. Therefore, intersecting ruggedness (recess-and-projection) patterns are formed in the surface of the guide wire 10 by the grooves 71 in both the die rollers 70. Specifically, by the grooves 71 arranged orthogonally to each of the rotational axes, helical ruggedness (recess-ang-projection) patterns corresponding to the crossing angle of the rotational axes are formed. More specifically, a net-like pattern as shown in FIG. 18 is formed.

In this way, the ruggedness (recess-and-projection) pattern(s) formed in the surface of the guide wire 10 can be modified by appropriately modifying the surface patterns of the first die roller and the second die roller.

(Third Embodiment)

In a third embodiment, a mode in which the methods and apparatuses for manufacturing a guide wire in the first embodiment and the second embodiment are further improved will be shown.

Figure 19:
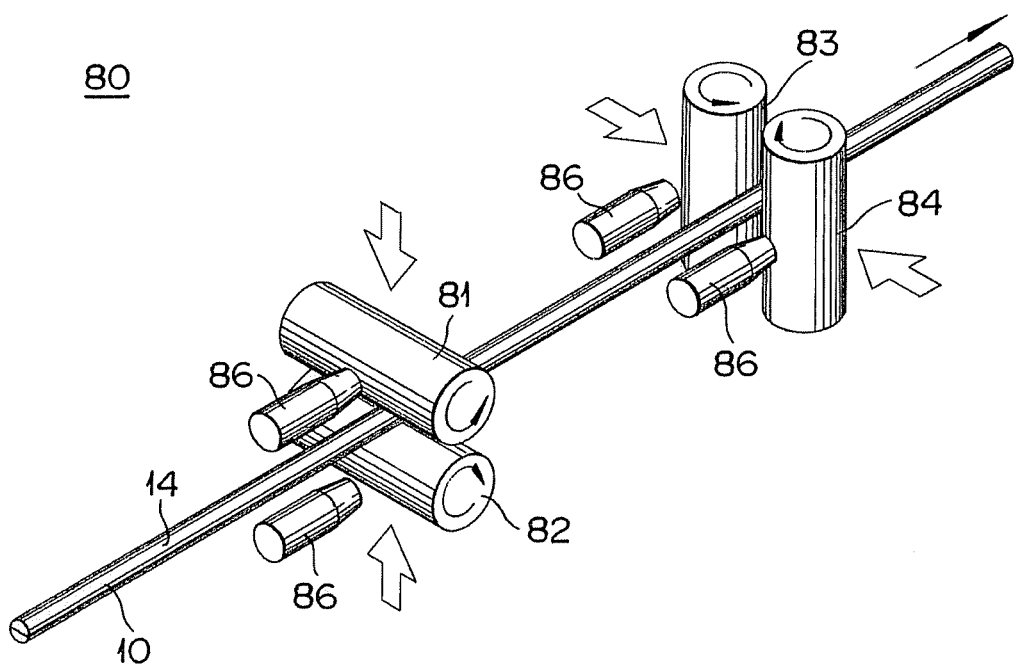
FIG. 19 illustrates an apparatus for manufacturing a medical elongate member.

FIG. 19 illustrates an apparatus for manufacturing a medical elongate member.

In this embodiment, a method and an apparatus for manufacturing a guide wire 10 as a medical elongate member will be described.

(Apparatus Configuration)

As shown in FIG. 19, the manufacturing apparatus 80 has a pair of die rollers 81, 82 and another pair of die rollers 83, 84. The die rollers 81 to 84 are each formed in a cylindrical shape, and are each rotatable about a rotational axis which is perpendicular to the axial direction of the guide wire 10. The rotational axes of the paired die rollers 81 and 82 (or the paired die rollers 83 and 84) are parallel. On the other hand, the rotational axes of the die rollers 81 and 83 are not parallel. In this embodiment, the rotational axes of the die rollers 81 and 83 are 90 degrees relative to each other.

Each of the die rollers 81 to 84 is provided with a plurality of recesses 85 in a cylindrical side surface thereof. The plurality of recesses 85 are distributed uniformly on the circumference of the surface of each of the die rollers 81 to 84. Specifically, the recesses 85 are uniformly distributed at least in the circumferential portions, brought into contact with the guide wire 10, of the die rollers 81 to 84. The shape of the recesses 85 may be any shape, like in the case of the recesses 63, 65 in the second embodiment shown in FIGS. 15A, 15B. It is to be noted here, however, that the recesses 85 in the die rollers 81 to 84 are preferably the same in shape. In addition, the recesses 85 in the die rollers 81 to 84 are preferably the same in distribution density.

In the embodiment below, a case where a tetragon-based pyramid is adopted as the shape of the recesses 85 will be described.

The die rollers 81 to 84 are each heated by a heating device 86 such as a glass torch. The heating temperature can be modified, as required, according to the material of the resin layer 14 of the guide wire 10 described later. The heating device 86 may be a heater embedded in the inside of each of the die rollers 81 to 84.

(Manufacturing Procedure)

First, a wire 10 having a resin layer 14 at a surface thereof (hereinafter referred to as "guide wire 10") is prepared.

A pair of die rollers 81, 82 and another pair of die rollers 83, 84 are arranged so that each pair of die rollers clamp the guide wire 10 therebetween.

The die rollers 81 to 84 are each heated by a glass torch 86 to a temperature of not lower than the glass transition point Tg (or, in the case of an amorphous resin, the softening point thereof) of the resin layer 14 at the surface of the guide wire 10.

The die rollers 81 to 84 are rotated respectively in the directions of arrows in FIG. 19. Attendant on this, the guide wire 10 is fed in the axial direction thereof. As a result, projections corresponding to the shape of recesses 85 of die rollers 81 to 84 are formed in the heated resin at the surface of the guide wire 10. Similarly, projections are formed in the surface of the guide wire 10 by recesses 85 of the die rollers 81 to 84.

Since the guide wire 10 is fed attendant on the rotation of the die rollers 81 to 84, the die rollers 81 to 84 are sequentially brought into contact with different positions of the surface of the guide wire 10. Consequently, the projections are successively formed in the surface of the guide wire 10.

(Effects)

As above-described, according to the third embodiment, by passing the guide wire 10 between the die rollers 81 to 84, the projections 144 corresponding to the recesses 85 formed in the surface of each of the die rollers 81 to 84 are formed in the surface of the guide wire 10. Therefore, with the above-mentioned method and apparatus employed, very good productivity is ensured even when the medical elongate member such as a guide wire is comparatively long.

In addition, since the two pairs of die rollers 81, 82 and 83, 84 with a difference of 90 degrees being present between the directions of the rotational axes of the pairs are provided, the guide wire 10 is pressed uniformly from the whole circumference thereof. Therefore, the guide wire 10 is not rotated during working, and uniform rugged (recess-and-projection) surface patterns can be formed.

The die rollers 81 to 84 each form a rectilinear rugged surface pattern in the surface of the guide wire 10. According to the one pair of die rollers 81, 82 and another pair of die rollers 83, 84 with the 90-degree shift between the rotational axes, four rugged surface patterns are formed in the surface of the guide wire 10 at regular angular intervals of 90 degrees. In order to form the rugged surface patterns on the whole circumference of the guide wire 10, the guide wire 10 is rotated by six degrees, for example, and is then passed again between the die rollers 81 to 84, whereby the patterns are transferred to the whole circumference of the guide wire 10.

The recesses 85 in the die rollers 81 to 84 are formed in the shape of a pyramid, a cone, a truncated pyramid or a truncated cone. Particularly, when the inclination angle A of the side surfaces of the recesses relative to the major surface of each of the die rollers 81 to 84 is not more than 60 degrees, there is not edge that hooks the resin having entered the recesses 85. This ensures when the recesses 85 part from the guide wire 10, there is no possibility that the projections formed in the resin surface 14 at the surface of the guide wire 10 might be caught (hooked) on edges and broken. Consequently, the peel strength of the projections is enhanced.

Since the die rollers 81 to 84 are being heated, the shape of the recesses 85 can be easily transferred to the resin of the resin layer 14.

(Modification Example of Die Rollers)

In the third embodiment above, the one pair of die rollers 81, 82 and another pair of die rollers 83, 84 have been used. However, the present invention is not limited to this configuration. For example, use of only one pair of die rollers may be adopted.

Or, three or more pairs of die rollers may also be employed. In this case, the positions of the die roller pairs are so adjusted that rugged surface patterns are formed in non-overlapping portions of the surface of the guide wire 10. Specifically, the die roller pairs are arranged so that the rotational axes of the die roller pairs are shifted at regular angular intervals. This ensures that by only passing the guide wire 10 between the plurality of pairs of die rollers, rectilinear rugged surface patterns the number of which is equal to the number of the die rollers can be formed at a time.

Consequently, the manufacturing time of the guide wire 10 can be shortened. For example, 24 pairs of die rollers are prepared. When the die roller pairs are arranged in the state of being shifted at regular angular intervals of 7.5 degrees, 48 rugged surface patterns can be formed at a time on the whole circumference of the guide wire 10.

(Catheter)

In the first to third embodiments above, examples in which projections are formed in the surface of the guide wire 10 have been described. However, the present invention is not limited to these examples. In the case of catheters to be used in a telescopic system, the catheter disposed on the inner side may be provided in its surface with projections which are distributed uniformly, like in the case of the guide wire 10 above.

Figure 20:
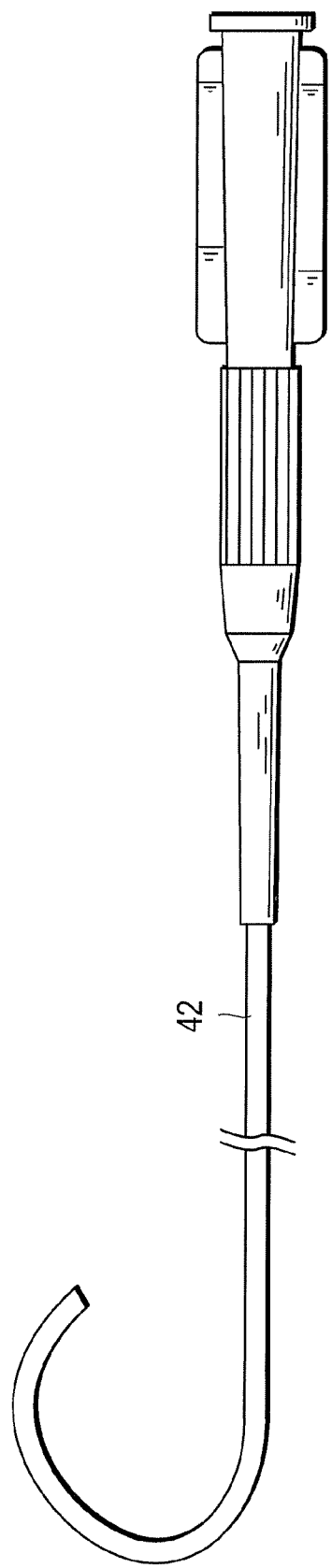
FIG. 20 is a schematic view of a catheter which is placed in the inside of a telescopic system.
Figure 21:
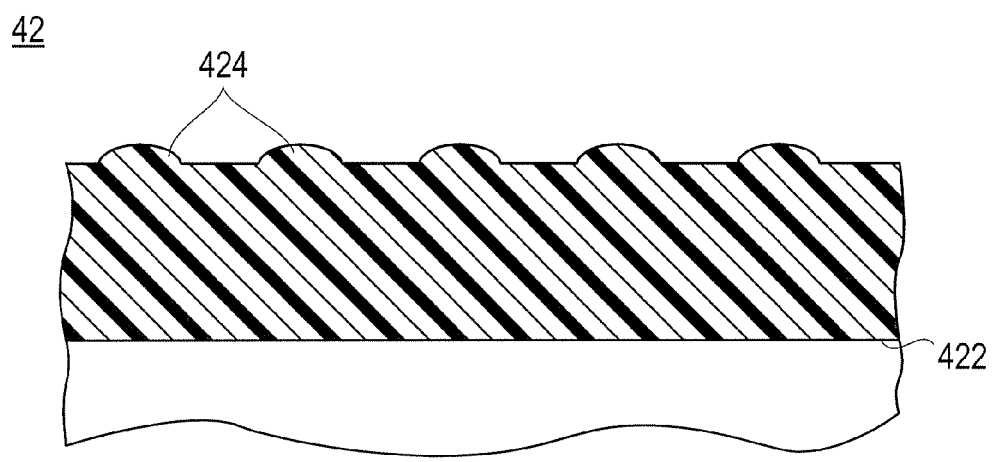
FIG. 21 is a partial sectional view of the surface of the catheter shown in FIG. 20.

FIG. 20 is a schematic view of a catheter placed in the inside of a telescopic system, and FIG. 21 is a partial sectional view of the surface of the catheter shown in FIG. 20.

The catheter 40 shown in FIG. 20 is for use in combination with another catheter, and is inserted in a lumen formed along the longitudinal direction of the another catheter. The catheter 40 has a tubular distal portion 42 which is flexible. The portion 42 is provided, in its substantially central part and over the whole length of the catheter body, with a lumen 422 so that a guide wire can be inserted therein. The distal portion 42 has a single-layer structure, and is formed of a resin.

The distal portion 42 is provided with projections 424 in its surface, as shown in FIG. 21. The projections 424 are formed by transferring the shape of a die, by a technique similar to that for the guide wire 10 described above. As above-mentioned, the projections 424 may be formed in any shape, such as a hemispherical shape, a truncated conical shape, a truncated pyramidal shape, and shapes obtained by forming finer projections in the surfaces of these shapes.

Incidentally, while the catheter 40 having a single-layer structure is shown here as a base material, this is not limitative. The catheter may be formed in a multilayer structure.

Figure 22:
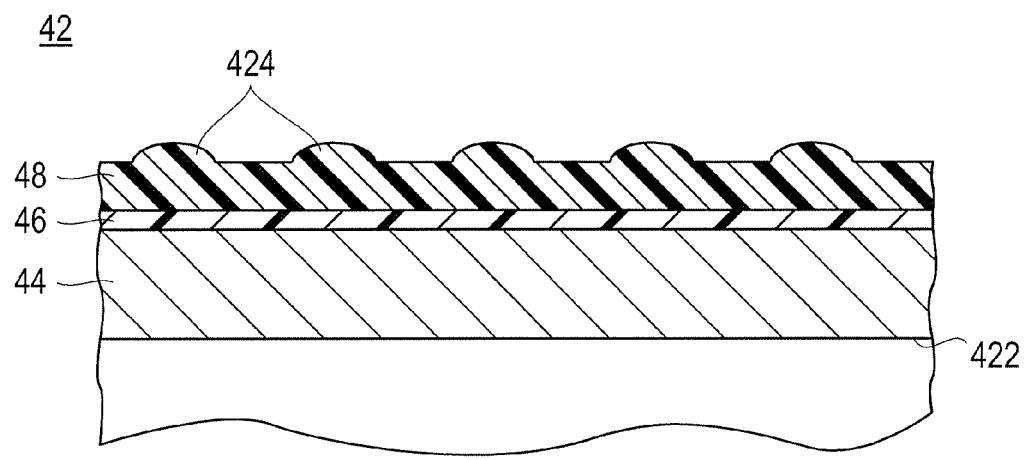
FIG. 22 is a partial sectional view of the surface of a catheter formed in a multilayer form.

FIG. 22 is a partial sectional view of the surface of a catheter formed in a multilayer structure.

A distal portion 42 of the catheter shown in FIG. 22 has a primer layer 46 provided on the surface of a base material 44, and a fluororesin layer 48 provided on the surface of the primer layer 46. The base material 44 is provided therein with a lumen 422 in which a guide wire can be inserted. The primer layer 46 and the fluororesin layer 48 are formed, for example, of resins or other flexible materials. Projections 424 are formed in the surface of the fluororesin layer 48.

When the projections 424 are formed on a surface of the catheter 40, a core material, for example including a metal wire, resin rod, gas of N2 or O2, volatile liquid, is preferably filled to the rumen 422.

Thus, the present invention is applicable not only to the guide wires 10 but also to any other medical elongate members such as a wire for medical use and the catheter 40. The present invention also may be applicable not only to the medical elongate members but also to any other members having needs for a uniformly low sliding resistance over the entire part thereof.

The entire disclosure of Japanese Patent Application No. 2007-338104 filed on Dec. 27, 2007, Japanese Patent Application No. 2008-015153 filed on Jan. 25, 2008, U.S. Provisional Patent Application No. 61/016,749, filed on Dec. 26, 2007, U.S. Provisional Patent Application No. 61/006,678 filed on Jan. 25, 2008, U.S. Provisional Patent Application No. 61/064,137 filed on Feb. 19, 2008 and U.S. Provisional Patent Application No. 61/064,332 filed on Feb. 28, 2008 including specifications, claims, drawings and summary are incorporated herein by reference in its entirety.

What is claimed is:

1. A method of manufacturing a medical elongate member, comprising the steps of:
   preparing an elongate member having a circumferential outer surface formed of a resin and a longitudinal axis;
   arranging a first die roller which is rotatable about a first rotational axis inclined against the axial direction of said elongate member and which is provided with recesses in a cylindrical side surface thereof and a second die roller which is rotatable about a second rotational axis inclined against the axial direction of said elongate member and crossing said first rotational axis and which is provided with recesses in a cylindrical side surface thereof, in such a manner as to clamp said elongate member between said first die roller and said second die roller;
   rotating said first and second die rollers while axially feeding said elongate member between said first and second die rollers so that said first and second die rollers by themselves impart the entire circumferential outer surface of said elongate member with a rugged surface pattern corresponding to said recesses in said first and second die rollers; and
   wherein said first rotational axis and said second rotational axis form acute crossing angles, which are not more than 10 degrees, with the longitudinal axis of said elongate member.

2. The method as set forth in claim 1, wherein said first rotational axis and said second rotational axis form equal crossing angles with the axis of said elongate member.

3. The method as set forth in claim 1,
   wherein the shape of said recesses in the surfaces of said first die roller and said second die roller is a pyramid or a truncated pyramid; and evenly arranged dot patterns are formed in the surface of said elongate member when said first die roller and said second die roller are rotated.

4. The method as set forth in claim 1, wherein said recesses in the surfaces of said first die roller and said second die roller are so shaped that the inclination angles of side surfaces of said recesses relative to the surfaces of said first die roller and said second die roller are each not more than 60 degrees.

5. The method as set forth in claim 1,
   wherein said recesses in said first die roller and said second die roller are grooves formed along the circumferential direction of the cylindrical side surfaces; and a net-like pattern is formed in the surface of said elongate member when said first die roller and said second die roller are rotated.

6. The method as set forth in claim 1, wherein said first die roller and said second die roller are each heated by a heating device.

7. A method of manufacturing a medical elongate member, comprising the steps of:
   preparing a solid elongate member having a surface formed of a resin;
   arranging a pair of die rollers each of which is rotatable about a rotational axis perpendicular to the axial direction of said elongate member and is provided with recesses in a cylindrical side surface thereof, in such a manner as to clamp said elongate member between said pair of die rollers, wherein the recesses are provided with finer recesses and air vents are formed at the finer recesses;
   providing said elongate member with a rugged surface pattern corresponding to said recesses and said finer recesses in said pair of die rollers by rotating said die rollers and feeding said elongate member in the axial direction thereof;
   wherein a plurality of said pairs of die rollers are arranged along the axial direction of said elongate member so that axially adjacent pairs of the die rollers are spaced apart from one another in the axial direction of the elongate member, the rotational axes of at least one pair of the die rollers being oriented in a different direction than the rotational axes of the die rollers of another of the pairs of die rollers; and
   passing said elongate member through said plurality of pairs of die rollers to form a plurality of said rugged surface patterns in non-overlapping portions of said elongate member.

8. The method as set forth in claim 7, wherein two said pairs of die rollers are prepared, the rotational axis of one of said two pairs of die rollers is set to be perpendicular to the rotational axis of the other of said two pairs of die rollers.

9. The method as set forth in claim 7, wherein the shape of said recesses in the surfaces of said die rollers is a pyramid or a truncated pyramid.

10. The method as set forth in claim 7, wherein said recesses in the surfaces of said die rollers are so shaped that the inclination angles of side surfaces of said recesses relative to the surfaces of said die rollers are each not more than 60 degrees.

11. The method as set forth in claim 7, wherein said die rollers are each heated by a heating device.

12. The method as set forth in claim 1, wherein said elongate member comprises a plurality of projections dispersed uniformly in a surface of said resin layer.

13. The method as set forth in claim 12, wherein said projections are provided with finer ruggedness in their surfaces.

14. The method as set forth in claim 1, wherein the surface of said resin has an SMD of 0.22 to 0.48 μm.

15. The method as set forth in claim 7, wherein said elongate member comprising a plurality of projections dispersed uniformly in a surface of said resin layer.

16. The method as set forth in claim 15, wherein said projections are provided with finer ruggedness in their surfaces.

17. The method as set forth in claim 7, wherein the surface of said resin has an SMD of 0.22 to 0.48 μm.

18. A method of manufacturing a medical elongate member possessing a circumferential outer surface, comprising:
   feeding the elongate member between a first die roller and a second die roller, the first die roller being rotatable about a first rotational axis inclined against the axial direction of said elongate member and being provided with recesses in a cylindrical side surface thereof, and the second die roller being rotatable about a second rotational axis inclined against the axial direction of said elongate member and crossing said first rotational axis and being provided with recesses in a cylindrical side surface thereof, the first and second die rollers being arranged in such a manner as to clamp said elongate member between said first die roller and said second die roller as the elongate member is fed between the first and second die rollers, wherein the recesses are provided with finer recesses and air vents are formed at the finer recesses; and
   providing the entire circumferential outer surface of said elongate member with a rugged surface pattern corresponding to said recesses and said finer recesses in said first die roller and said second die roller by rotating said first die roller and said second die roller while axially feeding said elongate member between the first and second die rollers wherein said elongate member comprises a plurality of projections dispersed uniformly in a surface of said resin, wherein the surface of said resin has an SMD of 0.22 to 0.48 μm.

19. The method as set forth in claim 18, wherein said projections are provided with finer ruggedness in their surfaces.

20. A method of manufacturing a medical elongate member, comprising the steps of:
   preparing an elongate member having a surface formed of a resin;
   arranging a first die roller which is rotatable about a first rotational axis inclined against the axial direction of said elongate member and which is provided with recesses in a cylindrical side surface of said elongate member and a second die roller which is rotatable about a second rotational axis inclined against the axial direction of said elongate member and crossing said first rotational axis and which is provided with recesses in a cylindrical side surface of said elongate member, in such a manner as to clamp said elongate member between said first die roller and said second die roller;
   providing a whole circumference of said elongate member with a rugged surface pattern corresponding to said recesses in said first die roller and said second die roller by rotating said first die roller and said second die roller and rotatably feeding said elongate member in the axial direction of said elongate member; and
   wherein said elongate member rotates while passing between said first die roller and said second die roller, and the rotation of the elongate member forms the rugged surface pattern on the whole circumference of said elongate member.

\* \* \* \* \*